(12) United States Patent
Bernaz

(10) Patent No.: US 7,367,981 B2
(45) Date of Patent: May 6, 2008

(54) DEVICE FOR DERMABRASION

(76) Inventor: Gabriel Bernaz, 5C route des Jeunes, 1227 Carouge (CH)

( * ) Notice: Subject to any disclaimer, the term of this patent is extended or adjusted under 35 U.S.C. 154(b) by 608 days.

(21) Appl. No.: 10/600,624

(22) Filed: Jun. 20, 2003

(65) Prior Publication Data

US 2004/0092959 A1 May 13, 2004

Related U.S. Application Data

(63) Continuation of application No. PCT/IB01/02665, filed on Dec. 24, 2001.

(30) Foreign Application Priority Data

Dec. 24, 2000 (EP) ................................. 00811254

(51) Int. Cl.
*A61B 17/50* (2006.01)
*A61H 1/00* (2006.01)
(52) U.S. Cl. ........................................ 606/131; 601/70
(58) Field of Classification Search ................ 606/131; 451/121, 354, 357; 173/216; 601/46, 67, 601/69, 70–72, 136–142
See application file for complete search history.

(56) References Cited

U.S. PATENT DOCUMENTS

| 2,867,214 A | 1/1959 | Wilson |
| 2,917,056 A | 12/1959 | Dolan |
| 3,169,536 A | 2/1965 | Caracciolo |
| 4,438,767 A | 3/1984 | Nelson |
| 4,643,207 A | 2/1987 | Grahame |
| 5,562,643 A | 10/1996 | Johnson |
| 6,017,351 A | 1/2000 | Street |
| 6,139,553 A | 10/2000 | Dotan |
| 6,569,002 B2 * | 5/2003 | Smith et al. ............... 451/357 |
| 6,629,983 B1 * | 10/2003 | Ignon ........................ 606/131 |

FOREIGN PATENT DOCUMENTS

| DE | 3740902 | 12/1988 |
| EP | 0806184 | 11/1997 |

* cited by examiner

*Primary Examiner*—Vy Q. Bui
(74) *Attorney, Agent, or Firm*—Sturm & Fix LLP

(57) ABSTRACT

Skin dermabrasion device by gently contacting the skin with an abrasive, comprising a handleable housing (10) and driving means for the abrasive. This device is intended in particular for cosmetic treatments of the epidermis called microepidermabrasion. The device comprises a curved abrasive surface (30) held by a support (32) mounted in or on the housing (10, 18) for an oscillatory motion allowing the oscillation of the curved abrasive surface (30) about its axis. A support surface (40) surrounds the abrasive surface (30) on at least two opposing sides leaving a gap to allow the oscillating motion. The device is arranged in such a way as to allow, by the application of the support surface (44) against the skin (50) and around the region of the skin to be treated, the gentle contact of this region of skin with the oscillating abrasive surface. Thus a microabrasion of the epidermis through the oscillation of the curved abrasive surface (30) lightly applied against the skin is achieved, thanks to the support surface (40) that prevents any injury or penetration beyond the epidermis.

19 Claims, 4 Drawing Sheets

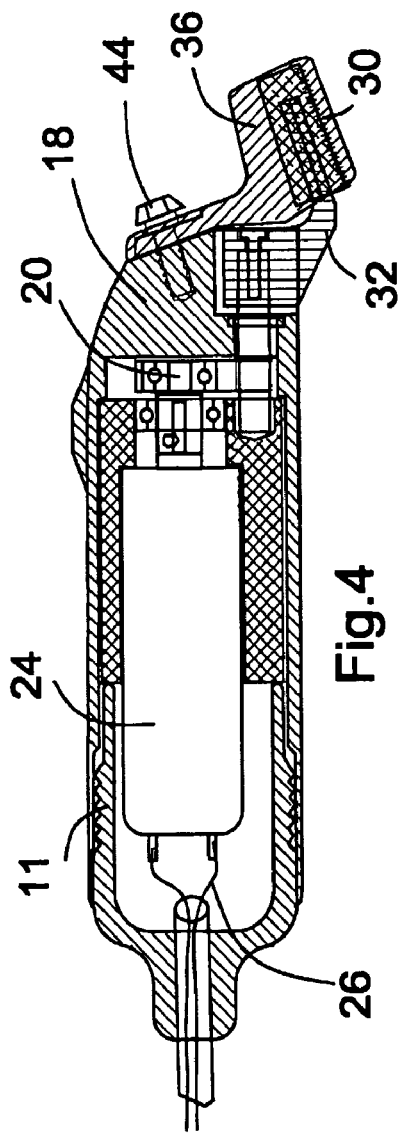
Fig.4
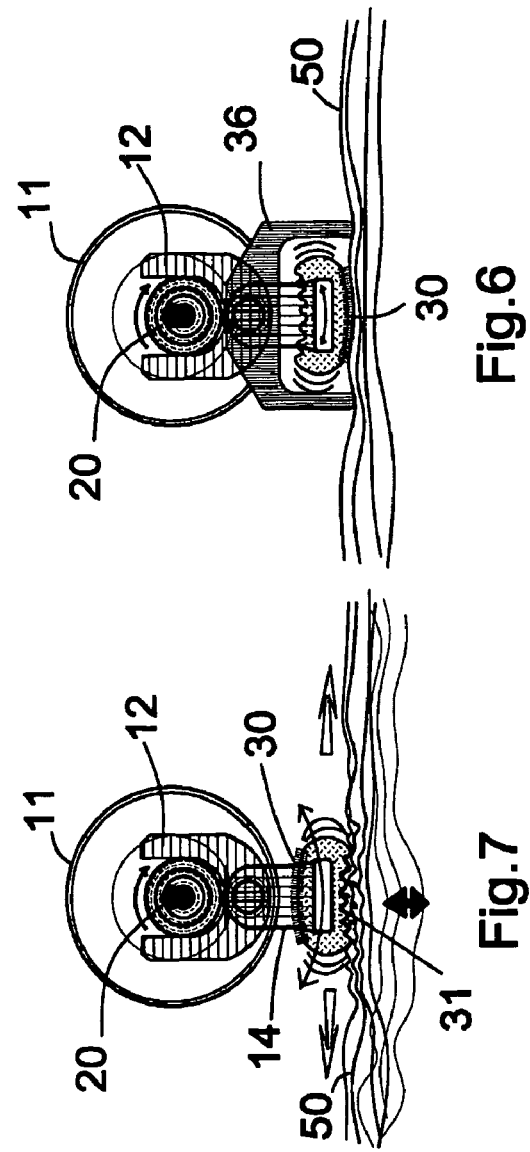
Fig.6
Fig.7
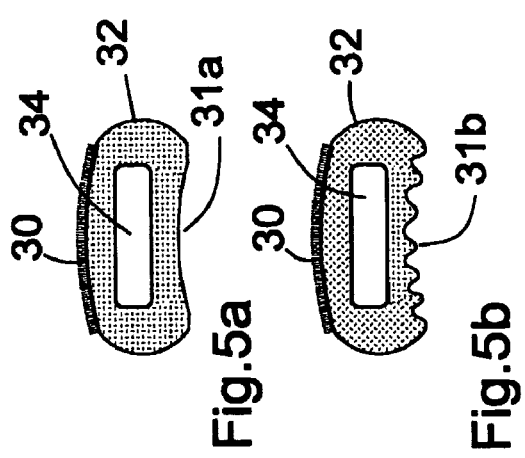
Fig.5a
Fig.5b

DEVICE FOR DERMABRASION

CROSS REFERENCE TO RELATED APPLICATIONS

This application is a Continuation application of PCT/IB01/02665 filed Dec. 24, 2001, claiming priority of European Application No. 00811254.2 filed Dec. 28, 2000, which are included in their entirety by reference made hereto.

TECHNICAL FIELD

The invention relates to the dermabrasion of the skin by placing the skin in gentle contact ("effleurage") with an abrasive, in particular for skin microepidermabrasion, that is to say the microabrasion of the superficial layer of the skin, or epidermis, which protects the deep part of the skin, or dermis, formed by a network of connective tissues containing vessels, nerves and follicles.

PRIOR ART

Microdermabrasion by the projection of aluminium hydroxide microcrystals is known for example from "La microdermabrasion en practique" by Francois Mahuzier (http://www.mahuzier.com) or also from "La Dermabrasion" by Dr. André Camirand (http://www.drcamirand.com), or also from "Dermabrasion & Dermaplaning" by the Canadian Plastic Surgery and Aesthetic Society (http://www.s-martnet.ca). These articles also mention dermabrasion by scratching with a metallic brush, or with a burin containing diamond particles, while dermaplaning uses an instrument called dermatome that includes an oscillating blade to remove the surface layers of the skin.

Microdermabrasion using the projection of corundum microcrystals is also described in publication EP-A-0 806 184.

Microdermabrasion by the projection of a liquid is known from the U.S. Pat. No. 5,562,643, while U.S. Pat. No. 5,562,643 describes microdermabrasion with the use of an ultrasonic tool, after the application of an anaesthetic.

U.S. Pat. No. 5,562,643 describes an apparatus for surgical microdermabrasion consisting of a plurality of flexible sheets having an abrasive edge rotating around a hub so as to strike the skin using centrifugal force.

These dermabrasion apparatus and processes are essentially intended for the abrasion of the skin down to the dermis, and generally necessitate a surgical intervention.

Cosmetic treatment of the epidermis using a handleable abrasive buffer of the type Scotch-Brite™ is known from U.S. Pat. No. 6,017,351, mainly for the purpose of removing excess dead skin.

U.S. Pat. No. 4,438,767 describes a handleable exfoliation blade, also for removing excess dead skin.

U.S. Pat. No. 4,643,207 concerns a manicuring device for removing the cuticle using an oscillating abrasive, and which includes a guiding device that penetrates under the cuticle in order to limit the penetration of the oscillating abrasive.

U.S. Pat. No. 2,917,056 describes an oscillating plate as an electric shaver accessory.

U.S. Pat. No. 6,139,553 describes a device for facial treatment, including an abrasive rotating disc, notably for causing the penetration of a treating product.

U.S. Pat. No. 2,867,214 describes a dermoplaning apparatus with a rotating brush the implementation of which includes a support to control the penetration depth of the rotating brush.

Document DE 37 40 902 describes a device with a rotating cylinder for the treatment of corns on the feet, the cylinder of which is surrounded by a support.

None of these apparatus is for skin dermabrasion and in particular microepidermabrasion.

SUMMARY OF THE INVENTION

This invention concerns a skin dermabrasion device using gentle contact ("effleurage") of the skin with an abrasive, the device comprising a handleable housing and abrasive driving means. This device is intended in particular for cosmetic epidermis treatments called microepidermabrasion.

The device according to the invention is characterized by the fact that it comprises, in combination, a curved abrasive surface held by a support mounted in or on the casing for an oscillating motion allowing oscillation of the curved abrasive surface around its axis, and a support surface surrounding the oscillating abrasive surface at least on two opposing sides leaving a gap to allow the oscillating motion of the abrasive surface. This device is arranged in such a way as to allow, by the application of the support surface against the skin and around the region of the skin to be treated, the gentle contact ("effleurage") of this region of the skin with the abrasive oscillating surface.

Thus a microabrasion of the epidermis by the oscillation of the curved abrasive surface lightly applied against the skin is achieved, thanks to the support surface that prevents any injury or penetration beyond the epidermis. The device is as easy to handle as an electric shaver, and allows the cosmetic microepidermabrasion of the skin for different treatments. It thus presents substantial advantages in relation to the known dermabrasion apparatus the use of which is limited to surgical or similar interventions, and which act as far as and into the dermis. Compared to manual apparatus for treating the epidermis, the new apparatus allows an automated treatment that is as easy on large surfaces as on small surfaces, and allows the carrying out of anti-wrinkle and other treatments that were not feasible with the known apparatus.

To promote the effect of microepidermabrasion, the curved abrasive surface does not project from the support surface, hence it is either at the level of this support surface, or advantageously arranged to be set back from the support surface, for example set back by 0 to 2 mm, usually at least about 1 to 1.5 mm, while the lateral gap between the curved surface and the edges of the support surface is usually about 1-4 mm on each side.

Advantageously, the abrasive surface is carried on a removable piece of rigid or flexible material on the oscillating support. Thus, the device can include several interchangeable pieces each with a different abrasive surface and/or of a different size. For example, one can have several interchangeable pieces having an identical abrasive surface, but with different lengths adapted to skin treatment on different parts of the body, and/or several interchangeable pieces with different abrasive surfaces designed to produce a more or less pronounced microabrasion.

The device according to the invention advantageously includes at least one double-faced removable piece mounted in a reversible way on the oscillating support, either with two different abrasive surfaces, or with a curved abrasive surface on one side and a smooth or rough massage surface on the other side, notably with a convex or flat profile and fitted with serrations or other protuberances. The latter removable piece thus allows the use of the dermabrasion device to carry out a massage by inverting the removable piece to use its rough oscillating surface, notably with the support surface removed and with a combined oscillating and vibration motion, as described below.

The piece equipped with the abrasive is made from rigid material, for example a molded plastic material, or from flexible material, for example a piece of flexible silicone that allows the application force of the abrasive on the skin to be adapted.

In one embodiment, the support surface is constituted by the edges of a U-shaped element which surround the piece fitted with the abrasive surface, this piece being removable through the open ends of the support surface's U-shaped element, hence facilitating exchange of the interchangeable pieces. The open end also allows the apparatus to be inclined for the treatment of recessed areas, such as wrinkle furrows.

The support surface of the device is constituted usually either of the edges of a removable element on the casing, or of the edges of the casing. In the latter case, the edges of the support surface constitute an integral part of the casing that is for example made of a molded thermoplastic.

A device whose support surface is positioned on a removable element presents the possibility of being used additionally with the support surface dismantled, to treat the parts of the body where the use of a support surface is not required. In particular, manicures and chiropody can be mentioned, also dermabrasion followed by massage.

Advantageously, the abrasive's driving means allow the variation of the oscillation speed of the abrasive surface whose oscillation speed can be between 0.5 to 200 oscillations per second, usually between 5-100 oscillations per second.

In one embodiment, these driving means include a pivoting mounted lever in the casing with an interdependent stirrup, the stirrup surrounding a cam driven by the shaft of an electric motor, the abrasive support being mounted at the pivoting end of the lever. In this case, the abrasive support oscillates with a swinging motion around its rotation axis, this rotation axis being positioned preferably between the cam and pivoting end of the lever, in such a way that the pivoting radius is reduced.

In general, this pivoting radius would be at the most approximately 20 mm, usually between 10-15 mm. In order to ensure a good microepidermabrasion effect the maximum oscillation amplitude is usually about 4 mm (2 mm on each side).

According to one embodiment, the oscillation axis of the curved surface is inclined in comparison with the housing axis, at an angle up to 25°, for example about 15° to 20°, which facilitates in particular its manipulation for certain treatments.

The above-mentioned embodiments can include a means for driving the abrasive support—or any other support, particularly for a rough massage surface—with a combined oscillation and vibration motion, through a reciprocation perpendicular to said oscillation motion, simultaneously with said oscillating motion or instead of it. This allows the incidental use of the dermabrasion device for carrying out a massage, particularly through the use of a massage accessory such as the above-mentioned removable double-faced piece having on one face a rough massage surface.

In another embodiment, the abrasive is positioned on a cylindrical support oscillated by adequate means. Such a cylindrical configuration allows the development of large oscillating surfaces, increasing the possibilities for application of the device. Furthermore, with an abrasive cylindrical support it is possible to position several isolated abrasive areas spaced from each other around the periphery of the cylinder, each zone corresponding to a cylinder oscillation angle. The cylinder is then indexable allowing the selection of the abrasive zone accessible within the support surface.

The invention equally concerns a process for cosmetic skin treatment using microepidermabrasion, using the device according to the invention, preferably after having applied a cleansing product to the skin surface to be treated. In fact, this microepidermabrasion exposes the skin tissue and renders this skin tissue better prepared for undergoing different treatments.

A cosmetic skin treatment process according to the invention advantageously includes a preliminary microepidermabrasion using the apparatus of the invention, followed by application on the thus-treated epidermis of a treating product that is made to penetrate the skin tissue by the application of a high frequency electromagnetic flux of energy and/or by applying electromagnetic laser radiation, for example according to the patents EP 0573618 and 0773744 and Patent No. application WO 99/49800, or by applying a "normal" light source.

This treatment is advantageously an anti-wrinkle treatment, for the area around the eyes, on the forehead, around the mouth, etc. However, other treatments are also possible for example depilation treatment, on the upper lip or on frown lines or on larger surfaces. Other treatments are the treatment of blemishes, stretch marks, acne and scars. It is also convenient for scalp treatments, particularly to allow the penetration of hair restoring products.

Finally, the invention also concerns the use of the device for skin microepidermabrasion and also for combined microepidermabrasion and massage treatments.

BRIEF DESCRIPTION OF THE DRAWINGS

Other characteristics of the invention will emerge from reading the description below, given by way of example, and referring to the drawings, in which:

FIG. 4 is a side view in axial cross-section of an embodiment where the oscillation axis is sloped in comparison with the axis of the casing;

FIGS. 5a and 5b are cross-sections of two reversible double-face support abrasive pieces;

FIG. 6 is a schematic view like FIG. 3 showing the reversible piece of FIG. 5b used for dermabrasion; and FIG. 7 is a schematic view like FIG. 6 showing the reversible piece of FIG. 5b used for massage, with the support surface removed.

PREFERRED EMBODIMENTS OF THE INVENTION

Figure 1:
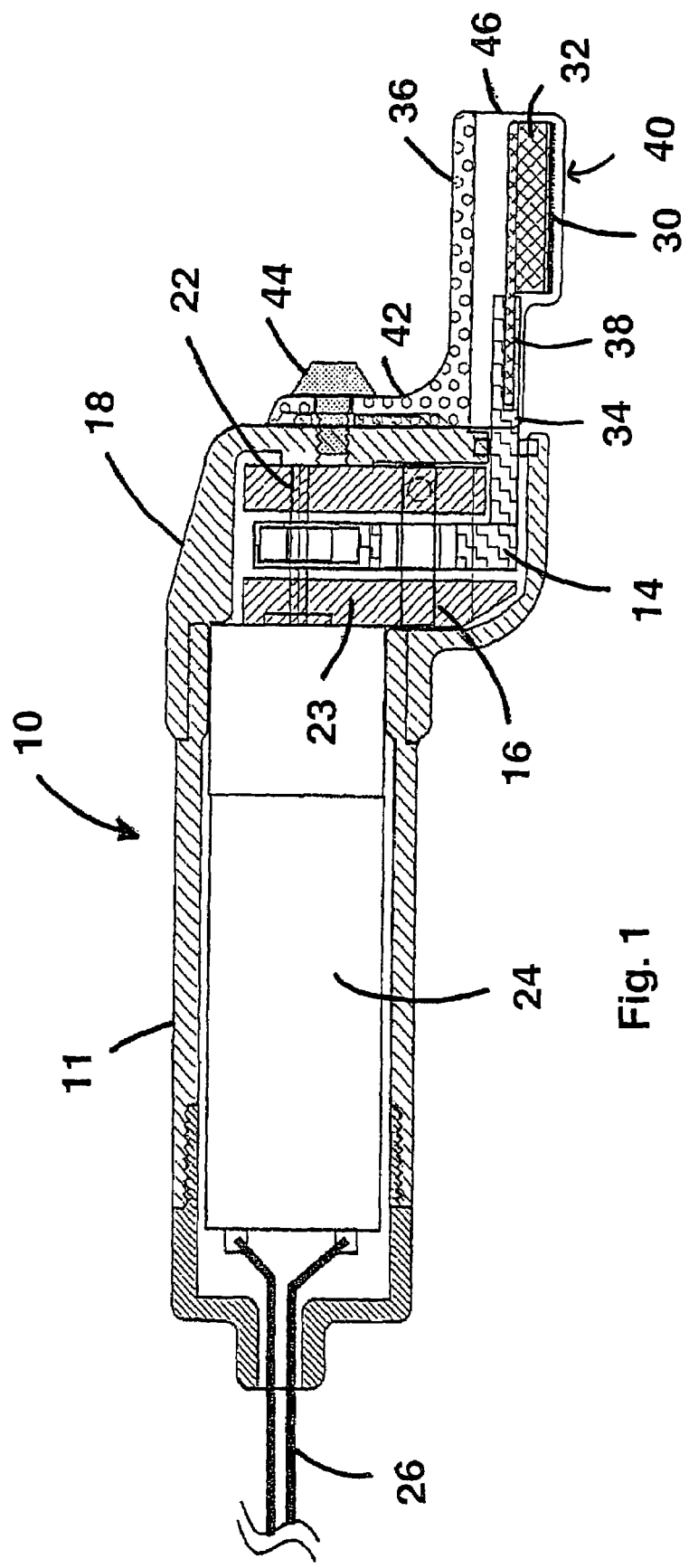
FIG. 1 is a side view in axial cross-section along line I-I of FIG. 2 of an embodiment of the device according to the invention.
Figure 2:
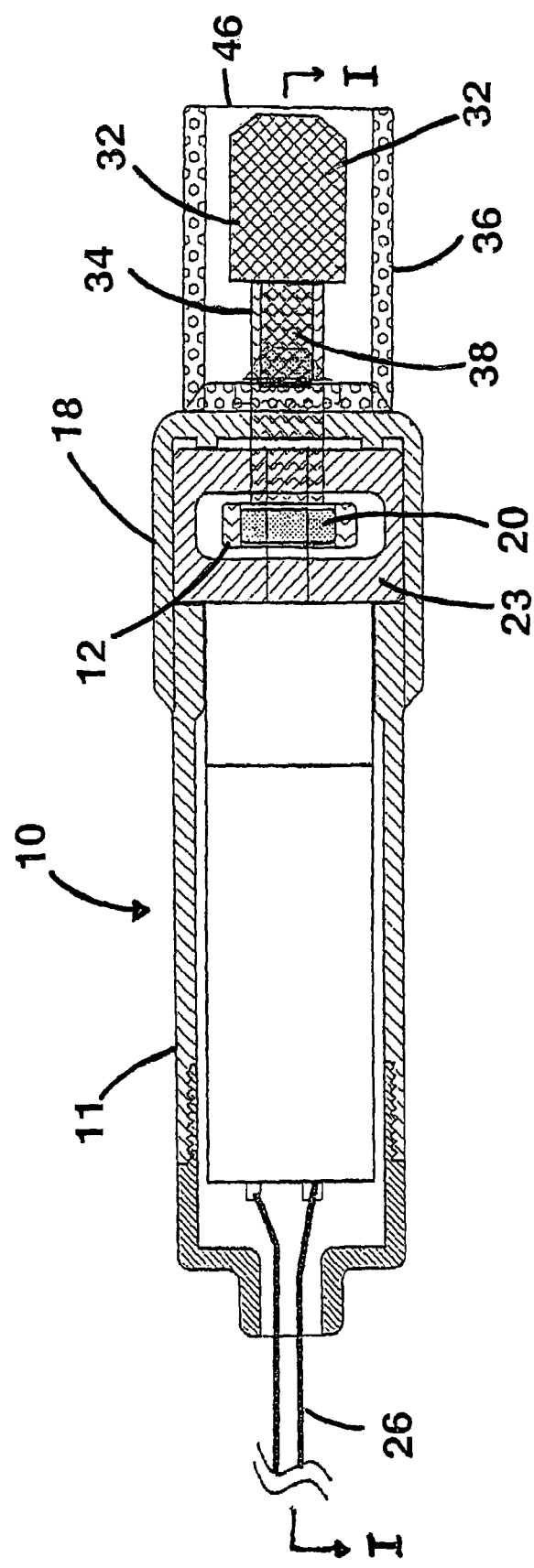
FIG. 2 is a schematic view in plan and cross-section of FIG. 1.
Figure 3:
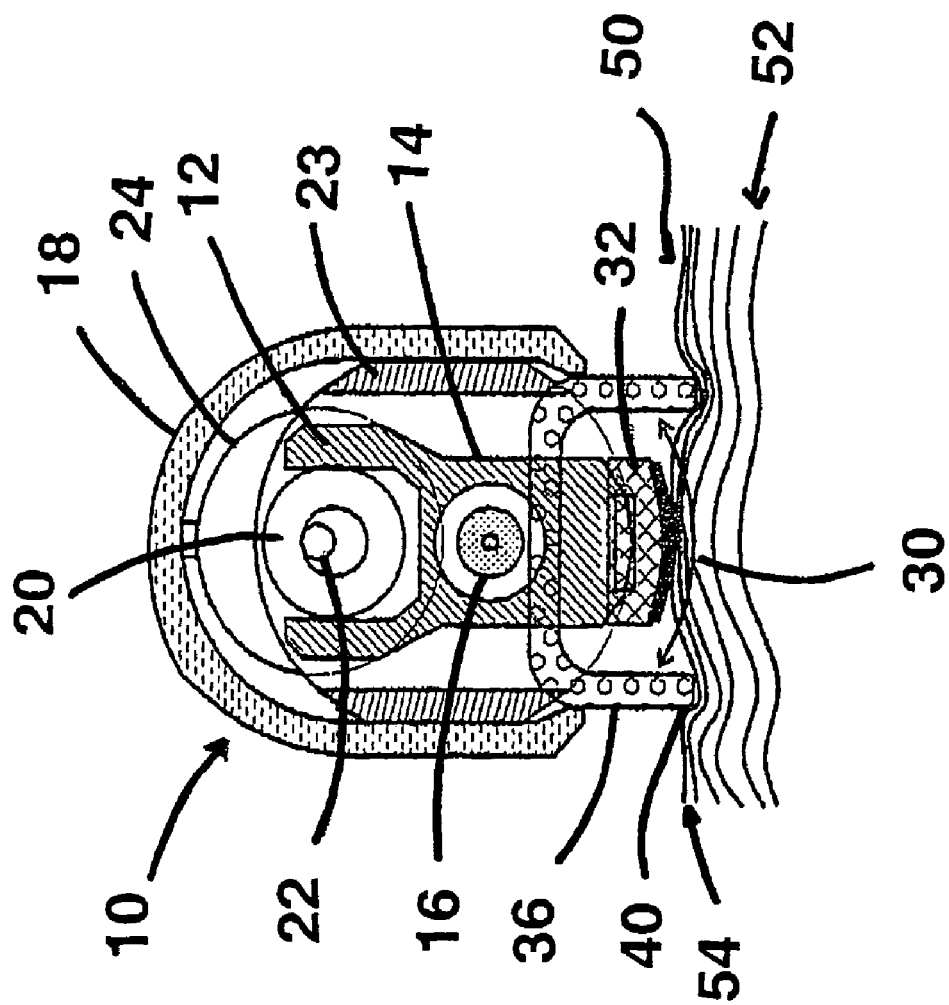
FIG. 3 is a side schematic cross-sectional view, showing the apparatus of FIGS. 1 and 2 in contact with the skin.

FIGS. 1 to 3 represent a skin dermabrasion device including a handleable housing 10 and driving means for an abrasive 30. In this embodiment, the driving means include a stirrup 12 solid with a lever 14 pivoting around an axis 16 in a casing 18 mounted onto one end of the elongated body of the housing 10. The two arms of the stirrup 12 surround a cam 20 driven by the shaft 22 of an electric motor 24 housed in the elongated body 11 of the housing 10.

The assembly of shaft 22, cam 20, lever 14, axis 16 is mounted in a mono-block body 23 housed in the casing 18.

The abrasive surface 30 is constituted by a curved surface of an elongate piece 32 removably attached on a support 34 mounted on the lower end of the lever 14, this piece 32 jutting out from the front end of the housing 10. The axis of this curved abrasive surface 30 coincides with the rotation axis 16 of the lever 14. Thus, the oscillation of the lever 14 produces a swinging oscillation of the curved abrasive surface 30 around its axis whose radius of curvature is between about 1-3 cm for example.

The abrasive-support piece 32 is made from for example a molded rigid plastic material, or from flexible silicone that allows adaptation of the force with which abrasive 30 is applied against the skin.

The motor 24 is supplied from the electric mains system by means of wires 26 carrying the current (and/or by an accumulator) and includes a speed variator allowing variation of the shaft 22 and cam 20's rotation speed, and thus the oscillation speed of the lever 14 and the abrasive surface 30. This abrasive surface 30 oscillates preferably at a speed between 0.5 to 200 oscillations per second, progressively variable or in stages, or possibly a single oscillation speed in this range, usually between 5 to 100 oscillations per second.

Furthermore, the device includes a support surface 40 constituted by the edges of a U-shaped element 36 that surround the abrasive-support piece 32. This element 36 surrounds three of the four sides of the oscillating abrasive surface 30 (see FIG. 2). This piece 32 includes a stem 38 removably mounted with a friction fit in a corresponding recess of the oscillating support 34.

The U-shaped element 36 includes a frontal part 42 serving to interlock this element 36 on the casing 18 by means of a screw 44, also allowing this element 36 to be removed if desired. Usually this element 36 remains in place, because it is necessary for security and for ensuring sufficient gentle contact ("effleurage") of the oscillating abrasive on the skin 50 to carry out a microepidermabrasion, without risk of penetrating the dermis 52.

When the element 36 is removed, it is still possible to use the device not for microepidermabrasion but for the abrasive treatment of parts of the body not requiring the protection provided by the support surface 40, for example for manicure and for chiropody and also for massage (FIG. 7).

The abrasive-support piece 32 is mountable and removable through the open end 46 of the U-shaped element 36, thus facilitating the exchange of interchangeable pieces 32. Other removable attachment means are possible.

The device advantageously includes several interchangeable pieces 32 each with a different abrasive surface 30, for example in sapphire powder or alumina, or another abrasive having a general grain size usually in the range of 50-200, suitably of about 80-120, and a hardness adapted for more-or-less pronounced microabrasion treatments. In general, an abrasive with a larger or finer grain will be used with a relatively low or high oscillation speed, respectively.

The interchangeable abrasive-support piece 32 can also be of different sizes, for example with different lengths adapted to the treatment of the skin of different parts of the body.

In this example, the curved abrasive surface 30 is set back in relation to the support surface 40, usually by at least about 1 to 1.5 mm, while the lateral gap between the curved surface and the edges of the U-shaped element 36 is about 1-2 mm on each side.

The use of the apparatus is very simple because the housing 10 is handleable, like an electric shaver. The application of the support surface 40 against the skin 50 to be treated, around the region of the skin to be treated, allows contact "effleurage" of the skin 50 with the oscillating abrasive surface 30 driven by the motor 24.

Thus a microabrasion of the epidermis 54 through the oscillation of the curved abrasive surface 30 lightly applied against the skin 50 is achieved, thanks to the support surface 40 that prevents any injury or penetration outside the epidermis 5. In general, the device is swept over the surface of the skin to be treated during a suitable time, usually during several minutes.

Usually the curved surface 30 will be applied flat on the skin 50, but for the treatment of wrinkle furrows and other recessed areas it is possible to incline the apparatus (towards the right of FIG. 1) and work using the pointed end of the abrasive, that is to say, the right end of FIG. 1. The working angle can thus vary from 0° up to approximately 45°.

FIG. 4, where the same references designate the same elements, shows an implementation of a dermabrasion device according to the invention where the oscillation axis is inclined in relation to the housing by about 20°, thus facilitating certain treatments. For this, the elongate piece 32 is bent and the U-shaped element 36 is mounted at an inclination on the casing 18 by means of the screw 44.

FIGS. 5a and 5b show in cross-section two abrasive support pieces 32 with a double reversible face, including on the one hand a curved abrasive surface 30 and, on the other hand, a lightly concave smooth surface 31a, or equipped with striations 31b, designed for a massage treatment.

FIG. 6 is a schematic view showing the reversible piece 32 of FIG. 5b used for dermabrasion, in this case with the U-shaped element 36 in position and with the oscillating abrasive surface 30, surrounded by the support surface 40, in contact with the skin 50, as in FIG. 3.

FIG. 7 shows the reversible piece 32 of FIG. 5b used for massage, with the U-shaped element 36 dismantled, i.e. without the support surface 40. In this case, piece 32 is mounted back to front, that is to say with the striated massage surface 31 in contact with the skin 50. Furthermore, in this implementation, the driving means of the oscillating support 34 (indicated in a schematic way in FIGS. 5a and 5b) is arranged to drive the support 34 in a to-and-fro oscillating motion perpendicular to the oscillating motion, simultaneously with said oscillating motion, as indicated by the arrows in FIG. 7. This oscillation will be produced by known means known as used in vibrators. This allows the incidental use of the device to carry out a massage, particularly following a dermabrasion treatment.

The device is preferably used to carry out a microepidermabrasion treatment after having applied a detergent lotion or other cleansing product to the surface of the skin 50 to be treated beforehand.

Microepidermabrasion using the apparatus can be followed by the application on the treated epidermis 54 of a gel or other treating product, for example an anti-wrinkle gel that is made to penetrate the skin tissue 50 through the application of a high frequency electromagnetic flux of energy and/or by the application of a coherent electromagnetic laser radiation, for example according to patents EP 0573618 and 0773744, or of continuous light in the colors blue-green-yellow-red of the rainbow of the visible spectrum. A treatment using a laser source, for example according to Pat.No. application WO/9949800, and/or a LED or other source of colored light, is particularly suitable, in particular a treatment for several minutes with the successive application of two or several laser sources or light sources of different energies. Such an anti-wrinkle treatment has given spectacular results after a total processing time of 10 to 20 minutes.

Other applications are the treatment of blemishes, stretch marks, acne, scars, depilation or scalp treatments, whereas when the support surface is removed other secondary treatments are possible for example manicures, chiropody and massage.

In general, the microepidermabrasion treatment significantly surpasses previous treatments. For treatments on large skin surfaces, it would be advantageous to use an abrasive surface positioned on an oscillating cylinder.

In place of a rotating motor, the driving means could comprise a reciprocating motor, like a vibrating device.

The invention claimed is:

1. Device for skin dermabrasion through gentle contact of the skin with an abrasive, the device comprising a handleable housing and abrasive driving means, wherein it comprises, in combination, an arcuate abrasive surface that extends along an arc of a cylindrical surface with the abrasive surface on the curved outside of the arc, the arcuate abrasive surface being held by a support mounted in or on the housing for an oscillatory motion caused by said driving means allowing oscillation of the arcuate abrasive surface about the axis of said cylindrical surface, and a support surface surrounding the oscillatory arcuate abrasive surface at least on two opposing sides, said axis of oscillation of the arcuate surface being parallel to said two opposing sides of the support surface, said two opposing sides leaving a gap to allow oscillating motion of the arcuate abrasive surface in said gap with the arcuate abrasive surface oscillable across the gap between said two sides, the device being arranged in such a way as to allow, solely by the manual application of the support surface against the skin and around the region of the skin to be treated, the gentle contact of this region of the skin with the oscillating arcuate abrasive surface.

2. Dermabrasion device according to claim 1, wherein the arcuate abrasive surface is at the level of the support surface or inset up to 2 mm relative to this surface, and wherein the lateral gap between the arcuate abrasive surface and the edges of the support surface is between 1 and 4 mm on each side.

3. Dermabrasion device according to claim 1, wherein the arcuate abrasive surface is carried on a piece of rigid or flexible material, said piece being removably mounted on the oscillating support.

4. Dermabrasion device according to claim 3, wherein it includes several interchangeable pieces each with a different arcuate abrasive surface and/or of a different size.

5. Dermabrasion device according to claim 4, wherein it includes at least one removable piece having a double face and mounted in a reversible way on the oscillating support.

6. Dermabrasion device according to claim 5, wherein the removable piece has on one side an arcuate abrasive surface and on the other side a massage surface.

7. Dermabrasion device according to claim 3, wherein the support surface is constituted by the edges of a U-shaped element that surround the piece with the abrasive surface, this piece being removable through the open end of the U-shaped element of the support surface.

8. Dermabrasion device according to claim 1, wherein said support surface is constituted by the edges of an element removably-mounted on the housing.

9. Dermabrasion device according to claim 1, wherein said support surface is constituted by the edges of the housing.

10. Dermabrasion device according to claim 1, wherein the driving means allow variation of the oscillation speed of the oscillating arcuate abrasive surface.

11. Dermabrasion device according to claim 1, wherein the oscillating arcuate abrasive surface has an oscillation speed between 0.5 to 200 oscillations per second.

12. Dermabrasion device according to claim 1, wherein the driving means comprise a stirrup solid with a lever mounted to pivot on the housing, the stirrup surrounding a cam driven by the shaft of an electric motor, said support of the abrasive arcuate surface being mounted at the end of the lever.

13. Dermabrasion device according to claim 1, wherein the oscillation axis of the arcuate surface is inclined to the axis of the housing.

14. Dermabrasion device according to claim 1, wherein the oscillatory support carrying the abrasive is cylindrical and has at least one arcuate abrasive surface on its cylindrical surface.

15. Process for cosmetic skin treatment by microepidermabrasion, using the device according to claim 1, comprising applying the support surface of the device against skin around a region of the skin to be treated, oscillating the arcuate abrasive surface about its axis and allowing, solely by the manual application of the support surface against the skin, the oscillating abrasive on the arcuate surface to gently contact the skin to treat the skin's epidermis.

16. Process according to claim 15, wherein a cleaning product is applied beforehand to the skin to be treated.

17. Process for cosmetic skin treatment including a preliminary microepidermabrasion according to claim 15, followed by application on the thus-treated epidermis of a treating product that is made to penetrate the skin tissue by the application of a high-frequency flux of electromagnetic energy and/or by the application of electromagnetic laser radiation and/or by light.

18. Process according to claim 15, for an anti-wrinkle treatment, treatments for blemishes, stretch marks, acne, scars, depilation or for scalp treatment.

19. Process according to claim 15 for skin microepidermabrasion.

* * * * *